United States Patent [19]

Omura et al.

[11] Patent Number: 4,812,558
[45] Date of Patent: Mar. 14, 1989

[54] TRIAZINE COMPOUND HAVING TWO VINYLSULFONE TYPE FIBER REACTIVE GROUPS

[75] Inventors: Takashi Omura, Ashiya; Kazufumi Yokogawa, Minoo, both of Japan

[73] Assignee: Sumitomo Chemical Company, Limited, Osaka, Japan

[21] Appl. No.: 119,333

[22] Filed: Nov. 10, 1987

[30] Foreign Application Priority Data

Nov. 19, 1986 [JP] Japan .................................. 61-275674
Feb. 20, 1987 [JP] Japan .................................. 62-38300

[51] Int. Cl.⁴ .................. C07D 251/12; C07D 251/16; C07D 251/26
[52] U.S. Cl. ........................................ 534/618; 534/624; 534/617; 534/632; 534/634; 534/637; 534/638; 534/642; 544/99; 544/187; 544/189; 544/193.1; 544/193.2; 544/208; 544/209; 544/211; 544/181; 544/197
[58] Field of Search .................. 544/189, 197, 193.1, 544/193.2, 211, 208, 99, 209, 181, 198, 187; 534/617, 618, 632, 634, 637, 638, 642, 624

[56] References Cited

U.S. PATENT DOCUMENTS 3,223,470 12/1965 Boedeker et al. .................. 544/189

FOREIGN PATENT DOCUMENTS 107614  5/1984 European Pat. Off. ............ 544/189
0182366 5/1986 European Pat. Off. ............ 534/618
0181585 5/1986 European Pat. Off. ............ 534/618
40-17113 8/1965 Japan ................................... 534/618

OTHER PUBLICATIONS

Chemical abstracts, vol. 101, 1984, p. 73, #112419d.

Primary Examiner—Mary C. Lee
Assistant Examiner—J. Richter
Attorney, Agent, or Firm—Stevens, Davis, Miller & Mosher

[57] ABSTRACT

A triazine compound having at least one symtriazine moiety of the following formula,

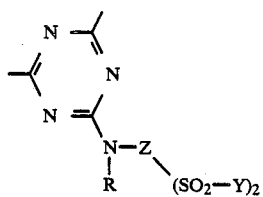

wherein R is hydrogen or unsubstituted or substituted alkyl, Y is vinyl or —CH$_2$CH$_2$L in which L is a group splittable by the action of an alkali, and Z is phenylene or naphthylene unsubstituted or substituted once by sulfo, which is useful for dyeing or printing fiber materials to give dyed or printed products of excellent fastness properties with superior dye performance, even when dyebath conditions including temperatures, pH, amounts of an inorganic salt and bath ratio are varied to some extent.

8 Claims, No Drawings

TRIAZINE COMPOUND HAVING TWO VINYLSULFONE TYPE FIBER REACTIVE GROUPS

The present invention relates to a triazine compound, a process for producing the same and a process for dyeing or printing fiber materials using the same. More specifically, the present invention relates to a triazine compound having two so-called vinylsulfone type fiber reactive groups a molecule, which is particularly useful for dyeing or printing fiber materials with superior dye performance.

Reactive dyes, particularly those having the vinylsulfone type fiber reactive group, have been extensively used for dyeing or printing fiber materials, because of their superior dye performance. For example, reactive dyes having both chlorotriazinyl and the vinylsulfone type fiber reactive groups are disclosed in the specification of the U.S. Pat. No. 3,223,470. However, these known reactive dyes are still insufficient to meet needs of high level for the dye performance including solubility, build-up property, washing-off property and insusceptibility to dyeing temperatures, as well as fastness properties including acid-hydrolysis fastness and chlorine fastness, and therefore these known dyes await improvements in these respects.

The present inventors have undertaken extensive studies to find a compound meeting such needs and satisfying various requisites in dyeing industries, and as a result found that a compound constituted in a manner such that a dye moiety, particularly anionic dye moiety, is most suitably combined with two vinylsulfone type fiber reactive groups through a specific bridging group can exhibit peculiar dye performance.

The present invention provides a triazine compound having at least one sym-triazine moiety of the following formula (I),

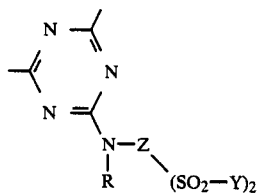
(I)

wherein R is hydrogen or unsubstituted or substituted alkyl, Y is vinyl (—CH=CH$_2$) or —CH$_2$CH$_2$L, in which L is a group splittable by the action of an alkali, and Z is phenylene or naphthylene unsubstituted or substituted once by sulfo.

More specifically, the present invention provides a triazine compound of the following formula (II),

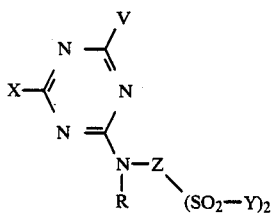
(II)

wherein R, Y and Z are as defined above, X is halogeno, C$_{1-4}$ alkoxy, unsubstituted or substituted aliphatic or aromatic amino, unsubstituted or substituted phenoxy, or a group of the formula (1),

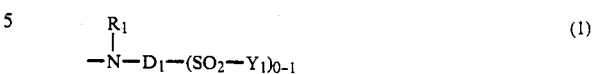
(1)

wherein R$_1$ is hydrogen or unsubstituted or substituted alkyl, D$_1$ is a dye moiety, and Y$_1$ is vinyl or —CH$_2$CH$_2$L in which L is as defined above, and V is a group of the formula (2)

(2)

wherein R$_2$ is hydrogen or unsubstituted or substituted alkyl, D$_2$ is a dye moiety, and Y$_2$ is vinyl or —CH$_2$CH$_2$L in which L is as defined above, or the formula (3),

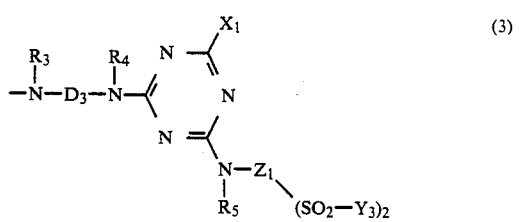
(3)

wherein R$_3$, R$_4$ and R$_5$ independently of one another are each hydrogen or unsubstituted or substituted alkyl, D$_3$ is a dye moiety, X$_1$ is halogeno, C$_{1-4}$ alkoxy, unsubstituted or substituted aliphatic or aromatic amino or unsubstituted or substituted phenoxy, Y$_3$ is vinyl or —CH$_2$CH$_2$L in which L is as defined above, and Z$_1$ is phenylene or naphthylene unsubstituted or substituted once by sulfo, or the formula (4),

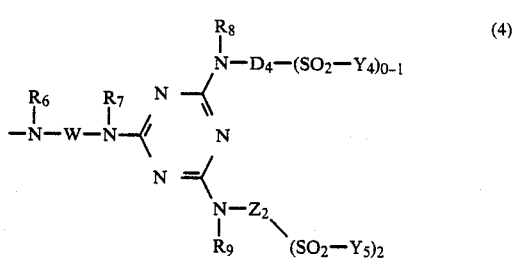
(4)

wherein W is a divalent group, R$_6$, R$_7$, R$_8$ and R$_9$ independently of one another are each hydrogen or unsubstituted or substituted alkyl, Z$_2$ is phenylene or naphthylene unsubstituted or substituted once by sulfo, D$_4$ is a dye moiety, and Y$_4$ and Y$_5$ independently of one another are each vinyl or —CH$_2$CH$_2$L in which L is as defined above.

Among these triazine compounds defined above, particularly preferred are those represented by the following formula (III) to (VI), the formula (III) being or substituted phenoxy, $Y_{11}$ and $Y_{12}$ independently of one another are each vinyl or $-CH_2CH_2L$ in which L is as defined above, $Z_5$ is phenylene or naphthylene unsubstituted or substituted once by sulfo, and $D_8$ is a dye moiety, and the formula (VI) being

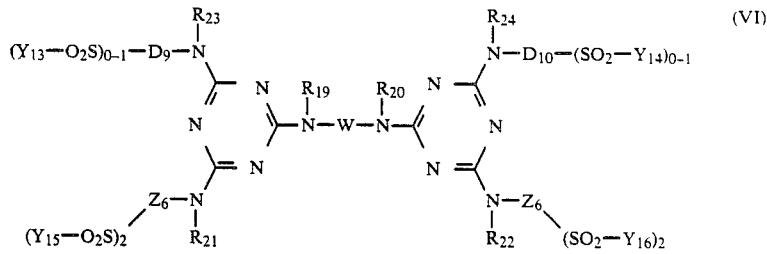

wherein $R_{19}$, $R_{20}$, $R_{22}$, $R_{23}$ and $R_{24}$ independently of one another are each hydrogen or unsubstituted or substituted alkyl, W is as defined above, $Y_{13}$, $Y_{14}$, $Y_{15}$ and $Y_{16}$ independently of one another are each vinyl or $-CH_2CH_2L$ in which L is as defined above, $Z_{16}$ is phenylene or naphthylene unsubstituted or substituted once by sulfo, and $D_9$ and $D_{10}$ independently of one another are each a dye moiety.

The present invention also provides a process for producing the triazine compounds as defined above, and a process for dyeing or printing fiber materials, which comprises using the triazine compounds as defined above.

In the present invention, the alkyl represented by R and $R_1$ to $R_{24}$ is preferably the one having 1 to 4 carbon atoms and unsubstituted or substituted with hydroxy, cyano, $C_{1-4}$ alkoxy, halogeno, carboxy, carbamoyl, $C_{1-4}$ alkoxycarbonyl, $C_{1-4}$ alkylcarbonyloxy, sulfo or sulfamoyl. Preferred examples of such alkyl are those described in Published Unexamined Japanese Patent Application No. 122549/1984. Particularly preferred R and $R_1$ to $R_{24}$ are, independently of one another, each hydrogen, methyl or ethyl. More specifically, at least one member of the group of $R_{10}$ and $R_{11}$, the group of $R_{12}$, $R_{13}$ and $R_{14}$, the group of $R_{17}$ and $R_{18}$, the group of $R_{21}$ and $R_{22}$, and the group of $R_{23}$ and $R_{24}$ is preferably hydrogen, and $R_{15}$ and $R_{16}$, and $R_{19}$ and $R_{20}$ are preferably the same, respectively.

Preferred examples of the divalent group represented by W are $C_{2-6}$ alkylene, phenylene mono- or disulfophenylene, 1,3,5-trimethyl-4-sulfo-2,6-phenylene, 6-substituted-1,3,5-triazine-2,4-di-yl, stilben-4,4'-di-yl and the like.

Among the substituents, halogeno, alkoxy, amino or phenoxy represented by X and $X_1$ to $X_4$, preferred are chloro, fluoro and anilino unsubstituted or substituted,

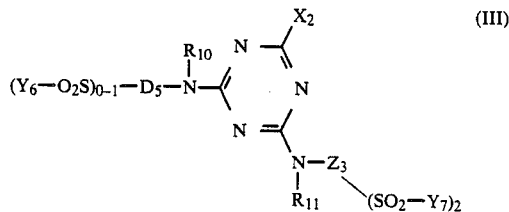

wherein $R_{10}$ and $R_{11}$ independently of one another are each hydrogen or unsubstituted or substituted alkyl, $X_2$ is chloro, fluoro, unsubstituted or substituted aliphatic or aromatic amino, $C_{1-4}$ alkoxy or unsubstituted or substituted phenoxy, $Y_6$ and $Y_7$ are independently of one another are each vinyl or $-CH_2CH_2L$ in which L is as defined above, $Z_3$ is phenylene or naphtylene unsubstituted or substituted once by sulfo, and $D_5$ is a dye moiety, the formula (IV) being

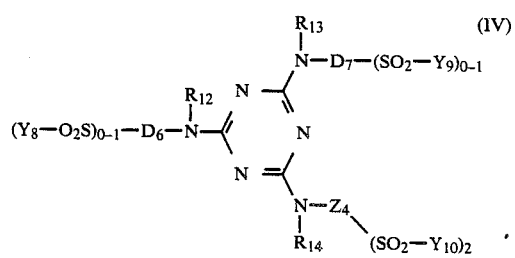

wherein $R_{12}$, $R_{13}$ and $R_{14}$ independently of one another are each hydrogen or unsubstituted or substituted alkyl, $Y_8$, $Y_9$ and $Y_{10}$ independently of one another are each vinyl or $-CH_2CH_2L$ in which L is as defined above, $Z_4$ is phenylene or naphthylene unsubstituted or substituted once by sulfo, and $D_6$ and $D_7$ independently of one another are each a dye moiety, the formula (V) being

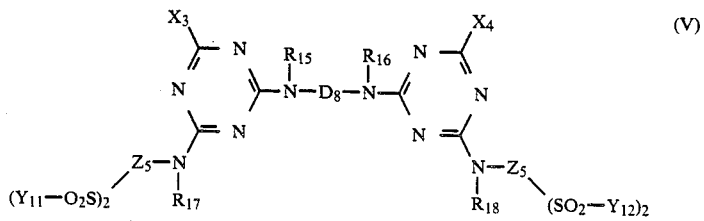

wherein $R_{15}$, $R_{16}$, $R_{17}$ and $R_{18}$ are independently of one another are each hydrogen or unsubstituted or substituted alkyl, $X_3$ and $X_4$ independently of one another are each chloro, fluoro, unsubstituted or substituted aliphatic or aromatic amino, $C_{1-4}$ alkoxy or unsubstituted for example, by sulfo, carboxy, chloro, $C_{1-4}$ alkyl and $C_{1-4}$ alkoxy. Although the symbols $X_3$ and $X_4$ may be different from each other, they are preferably the same from viewpoint of the production of the triazine compound represented by the formula (V).

The symbol L in —CH$_2$CH$_2$L represented by Y and Y$_1$ and Y$_{16}$ is a group splittable by the action of an alkali, and includes, for example, —OSO$_3$H, —SSO$_3$H, —PO$_3$H$_2$, —Cl and —OCOCH$_3$. Of these, preferred is —OSO$_3$H.

As the dye moiety represented by D$_1$ to D$_{10}$, preferred is an anionic dye moiety having —SO$_3$$^-$ as the anion. The anionic dye includes, for example, metal-containing or metal-free azo, anthraquinone, metal-containing phthalocyanine, metal-containing formazan, dioxazine and stilbene dyes. Of these dyes moieties, particularly preferred are those represented by the following formulas in each free acid form,

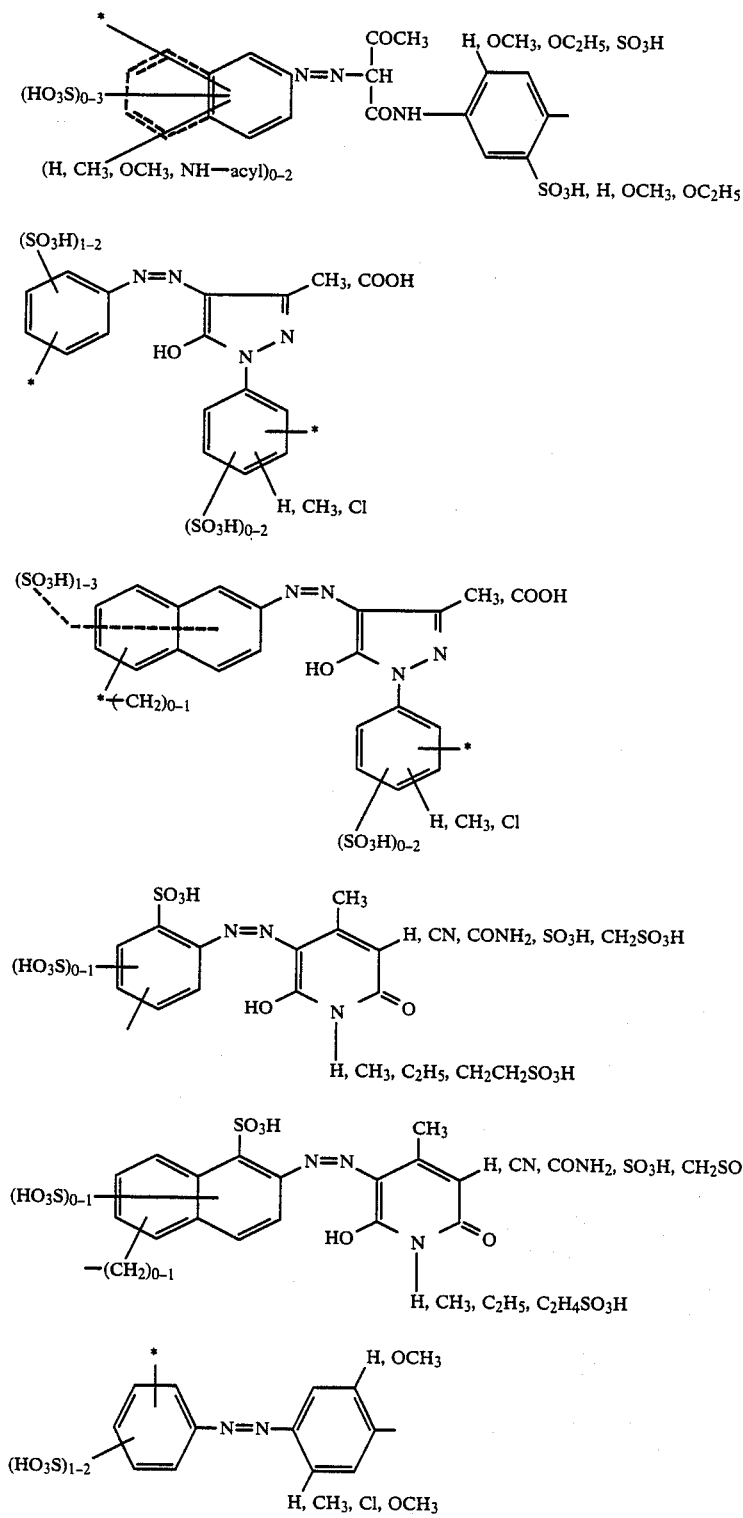

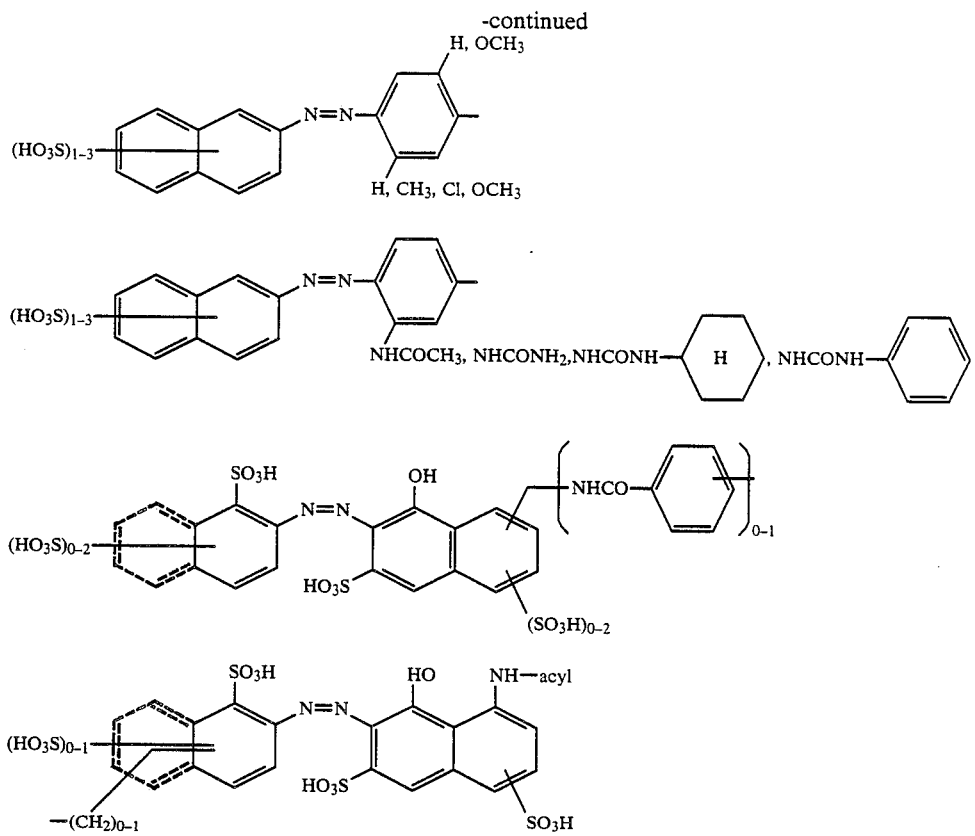
wherein acyl means acetyl or benzoyl unsubstituted or substituted, for example, by sulfo, carboxy, chloro, nitro and $C_{1-4}$ alkyl,
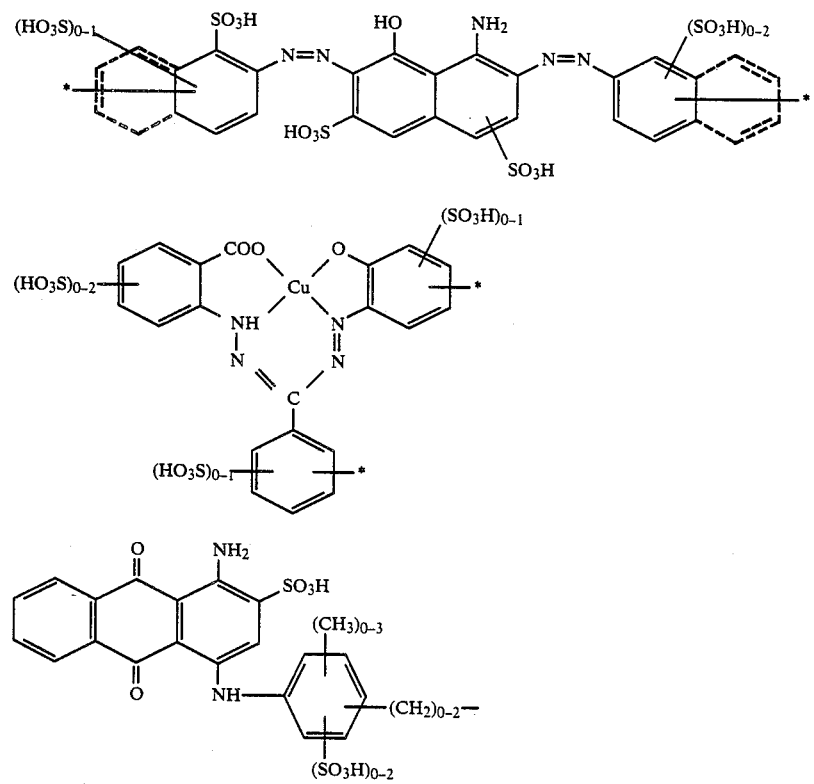

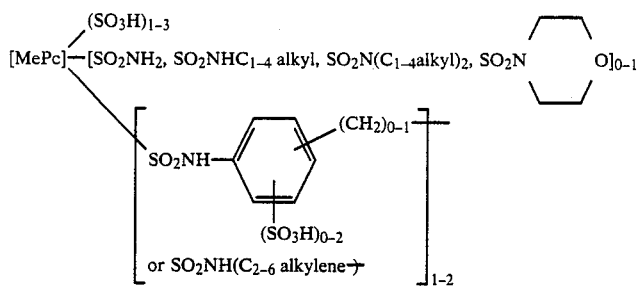
wherein MePc is Cu- or Ni-phthalocyanine residue, and an average substituent number of the said metal phthalocyanine is from 3 through 4,
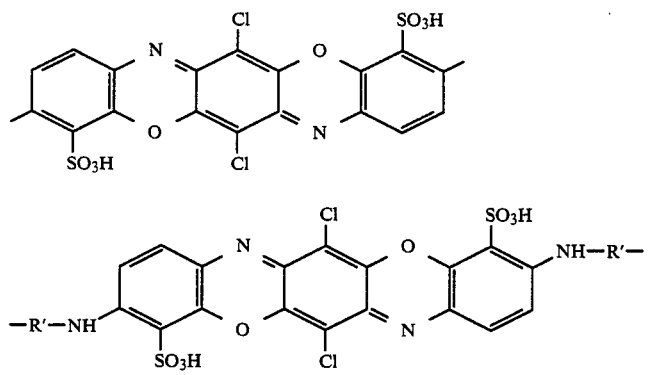
wherein R' is an aliphatic or alicyclic residue, such as
—(CH$_2$)$_{2-6}$—, —CH—(CH$_2$)$_{1-4}$—, —C$_2$H$_4$OC$_2$H$_4$—, —C$_2$H$_4$SC$_2$H$_4$—, —C$_2$H$_4$NC$_2$H$_4$—, —CH$_2$CHC$_2$H$_5$
      |                      |       |
      COOH                   COCH$_3$ C$_2$H$_4$OC$_2$H$_4$— , 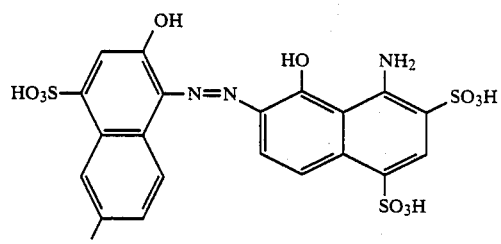 and
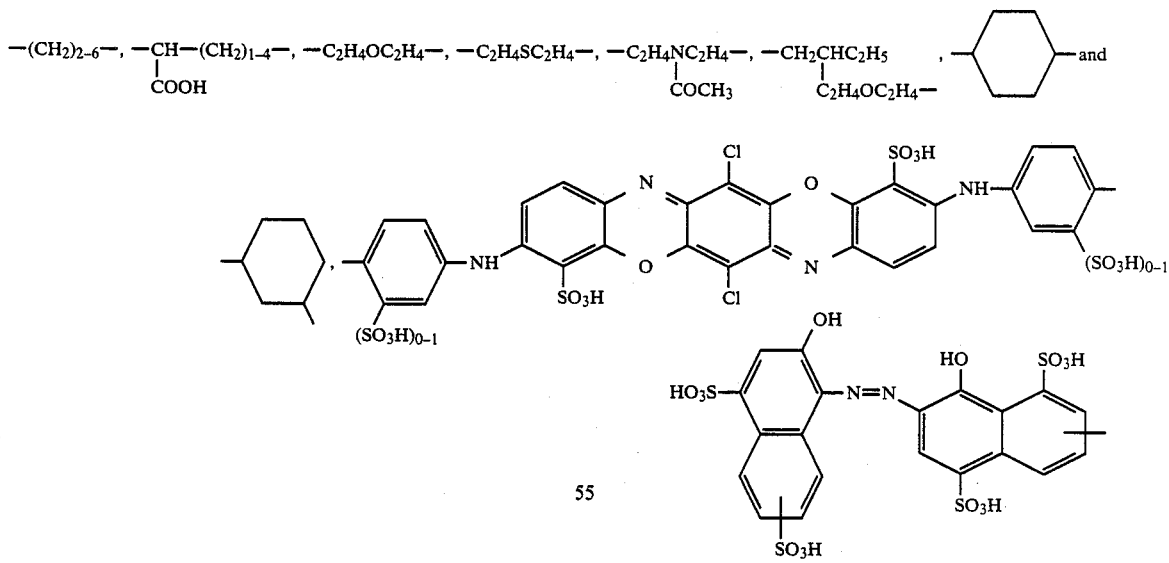
and metal complexes of the followings,
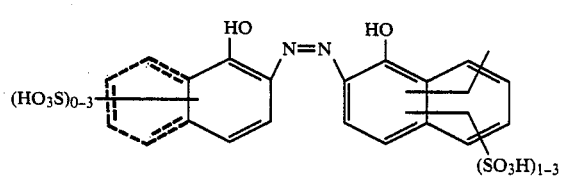

wherein preferred are 1:1-Cu, 1:2-Cr and 1:2-Co complexes.

The anionic dye moieties exemplified above are of mono- or di-valent. Examples of the dye moieties applicable to those represented by $D_5$ to $D_{10}$ in the formulas (III) to (VI) are those equal in the respective valent number. For this purpose, the asterisked linkage, or one of the two may bond to hydrogen to form the corresponding monovalent dye moiesties, which are also included in the present examples of the anionic dye moieties.

The respective fiber reactive groups, for example, expressed by —$SO_2$—Y in the formulas (I) and (II), are preferably located at 2,3-, 2,4-, 2,5- or 3,4-positions of the phenylene represented by Z, provided that the imino group,

is located at 1-position. When Z is naphthylene or sulfonaphthylene, examples of those carrying the fiber reactive groups are as follows:

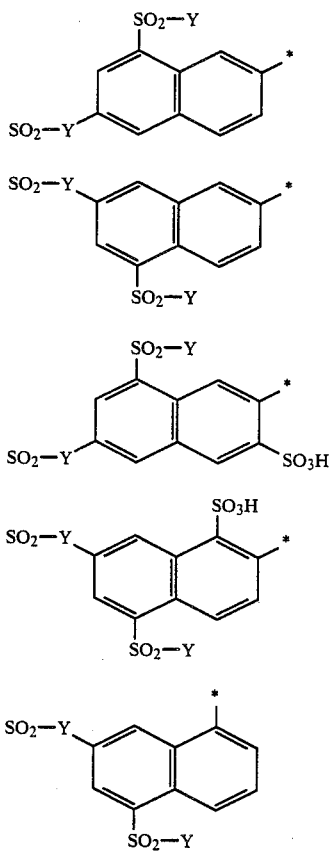

In the above formulas, Y is as defined above and the asterisked linkage bonds to the imino group,

For the production of the triazine compound represented by the formula (I), the starting compounds including a cyanuric halide such as cyanuric chloride and cyanuric fluoride, and a compound of the following formula (a),

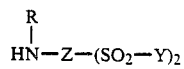

wherein R, Y and Z are as defined above, are allowed to condensation reactions with one another.

More specifically, for the production of the triazine compound represented by the formula (II), the starting compounds include (i) the cyanuric halide, (ii) the compound of the formula (a), (iii) any one of a compound of the following formula (b), $$X'H \quad (b)$$

wherein X' is halogeno, $C_{1-4}$ alkoxy, unsubstituted or substituted aliphatic or aromatic amino, or unsubstituted or substituted phenoxy, and a compound of the following formula (c),

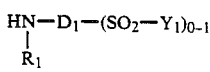

wherein $R_1$, $D_1$ and $Y_1$ are as defined above, and (iv) a compound of the following formula (d),

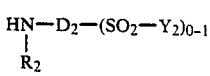

wherein $R_2$, $D_2$ and $Y_2$ are as defined above, or a group consisting of compounds of the following formulas (e), (f) and (g),

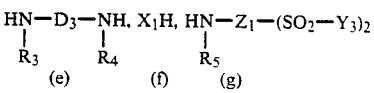

wherein $R_3$, $R_4$, $R_5$, $D_3$, $X_1$, $Y_3$ and $Z_1$ are as defined above, or a group consisting of compounds of the following formulas (h), (i) and (j),

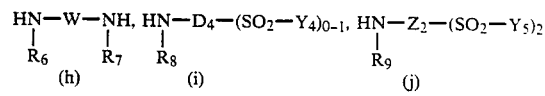

wherein $R_6$, $R_7$, $R_8$, $R_9$, $D_4$, W, $Y_4$, $Y_5$ and $Z_2$ are as defined above.

In the production of the triazine compound represented by the formula (II), the starting compounds described above can be subjected to condensation reactions in a manner known by the skilled person in this art.

The triazine compound in accordance with the present invention may be preferably in the form of alkali metal or alkaline earth metal satls, particularly sodium or potassium salt.

After completion of the reaction, the desired triazine compound-containing reaction mixture may be formed into a liquid commercial product, if desired, after removing inorganic salts and with addition of a stabilizer or a dyeing improver. The liquid product obtained or the aforesaid reaction mixture may be subjected to evaporation or spray-drying, thereby obtaining a pulverulent commercial product. Alternatively according to a conventional manner, the reaction mixture may be formed into either a liquid or pulverulent commercial product through a salting-out using an electrolyte.

The triazine compound (I) of the present invention is fiber-reactive and useful for dyeing or printing hydroxyl group-containing and amide group-containing materials.

The hydroxyl group-containing materials include natural or synthetic hydroxyl group-containing materials such as cellulose fiber materials, regenerated products thereof and polyvinyl alcohol. Examples of the cellulose fiber materials are cotton and other vegetable fiber such as linen, hemp, jute and ramie fibers. Examples of the regenerated cellulose fibers are viscose staple and filament viscose.

The amide group-containing materials include synthetic or natural polyamide and polyurethane. Examples of the materials, particularly in the fibrous forms, are wool and other animal furs, silk, leather, polyamide-6,6, polyamide-6, polyamide-11 and polyamide-4.

The dyeing may be carried out in a suitable manner, which can be selected from conventional manners depending on the physical and chemical properties of said fiber materials.

For example, cellulose fiber materials can be dyed using the triazine compound by an exhaustion dyeing, padding including cold batch-up dyeing or printing method.

The exhaustion dyeing can be carried out at a relatively low temperature in the presence of an acid binding agent such as sodium carbonate, trisodium phosphate, sodium hydroxide and the like, if desired, using a neutral salt such as sodium sulfate, sodium chloride and the like, together with hydrotropic agent, a penetrant or a level dyeing agent. The neutral salt usable for promoting the exhaustion may be added to a dye bath before or after temperature reaching a desired level for the dyeing, if desired, dividedly.

The padding can be carried out by padding the fiber materials at ambient temperature or an elevated temperature, and after drying, steaming or dry-heating the materials to perform the dye-fixation.

The cold batch-up dyeing can be carried out by padding the fiber materials with a padding liquor at ambient temperature, batching up and allowing them to stand on a roller for 3 hours or more or over night, followed by washing with water and drying.

The printing can be carried out in a one-phase or two-phase manner. The one-phase printing may be conducted by printing the fiber materials with a printing paste containing an acid binding agent such as sodium hydrogencarbonate and the like, followed by steaming at a temperature of 100° to 160° C. The two-phase printing may be conducted by printing the fiber materials with a neutral or weakly acidic printing paste, and passing the materials through a hot alkaline batch containing an electrolyte or over-padding the materials with an alkaline padding liquor containing an electrolyte, followed by a steaming or dry-heating treatment.

For the preparation of the printing paste, a stock paste or emulsifier such as sodium alginate, starch ether and the like may be used, if desired, together with a conventional auxiliary agent such as urea and/or dispersing agent.

The acid binding agent useful for fixing the compound of the present invention on the cellulose fiber materials includes water-soluble basic salts consisting of alkali or alkaline earth metals and inorganic or organic acids or compounds capable of liberating alkalis under heating conditions. Preferred are alkali metal hydroxides and alkali metal salts of inorganic or organic acids having a weak or medium strength. Particularly preferred are sodium salts and potassium salts. Examples thereof are sodium hydroxide, potassium hydroxide, sodium hydrogencarbonate, sodium carbonate, sodium formate, potassium carbonate, sodium dihydrogenphosphate, disodium hydrogenphosphate, trisodium phosphate, sodium silicate, sodium trichloroacetate and the like.

The dyeing of natural or synthetic polyamide and polyurethane fiber materials can be carried out by performing exhaustion in an acid or weak acid bath, while controlling the pH value, and then making the bath neutral, or in some cases alkaline to perform the fixation. The dyeing temperature ranges usually from 60° to 120° C. In order to achieve a level dyeing, there may be used a conventional level dyeing agent such as condensation product between cyanuric chloride and 3 times by mole of aminobenzene-sulfonic acid or aminonaphthalenesulfonic acid, or an addition product between stearylamine and ethylene oxide, and the like.

The present triazine compound can be characterized by excellent dye performance in the dyeing and printing of fiber materials, particularly cellulose fiber materials. For example, the triazine compound can exhibit high exhaustion and fixing percentages as well as excellent build-up property, and can give dyed or printed products excellent in wet fastness such as fastness to washing in the presence or absence of peroxides, fastness to alkali, acid, water or sea water, and the like, abrasion fastness, iron fastness, light fastness, perspiration-light fastness and perspiration fastness. Moreover, the triazine compound in accordance with the present invention is robust so that a shade to be obtained can hardly be affected by changes in dyebath conditions such as dyeing temperatures, pH, amounts of inorganic salts and bath ratios, and therefore dyed or printed products with a constant quality can be obtained with superior reproducibilty.

The present invention is illustrated in more detail with reference to the following Examples, which are only illustrative, but not limitative. In Examples, all parts and % are by weight.

EXAMPLE 1

Sodium salt of 1-amino-8-hydroxy-7-(o-sulfophenylazo)naphthalene-3,6-disulfonic acid (50.4 parts) was dissolved in water (500 parts), and cyanuric chloride (18.5 parts) was added thereto. The mixture was stirred at 0° to 5° C., while controlling the pH within 2 to 3, to complete a first condensation.

Successively, 1-aminobenzene-2,4-di($\beta$-sulfatoethylsulfone) (46.9 parts) was added to the above reaction mixture, and the resulting mixture was stirred at 40° to 50° C., while controlling the pH within 4 to 5, to complete a second condensation. Sodium chloride was added to the reaction mixture, and the precipitate was collected on a filter, washed and then dried to obtain a triazine compound of the following formula in a free acid form.

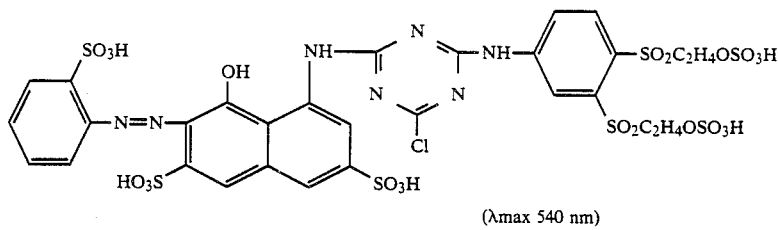

(λmax 540 nm)

EXAMPLE 2

Example 1 was repeated, provided that compounds as shown in columns A and B of the following table were used in place of 1-amino-8-hydroxy-7-(o-sulfophenylazo)naphthalene-3,6-disulfonic acid and 1-aminobenzene-3,4-di($\beta$-sulfatoethylsulfone), respectively, to obtain the corresponding triazine compound. In the right column, a shade of dyed product is shown. The symbol Q means $\beta$-sulfatoethylsulfonyl, which can be replaced by vinylsulfonyl or a group convertible into the vinylsulfonyl by the action of an alkali.

| No. | A | B | Shade |
|---|---|---|---|
| 1 | [structure: 2-sulfophenyl-azo-1-hydroxy-8-amino-naphthalene-3,5-disulfonic acid] | [2-Q, 4-Q, aniline] | Yellowish red |
| 2 | [structure: 1-sulfo-5-sulfo-naphthyl-2-azo-1-hydroxy-8-amino-naphthalene-3,5-disulfonic acid] | [2-Q, 4-Q, aniline] | Red |
| 3 | [structure: 2-sulfo-5-Q-phenyl-azo-1-hydroxy-8-amino-naphthalene-5-sulfonic acid] | [2-Q, 4-Q, aniline] | Red |
| 4 | [structure: 4-methoxy-2-sulfo-phenyl-azo-1-hydroxy-6-amino-naphthalene-3-sulfonic acid] | [2-Q, 4-Q, aniline] | Orange |
| 5 | [structure: 4-methoxy-2-sulfo-phenyl-azo-1-hydroxy-6-NHCH3-naphthalene-3,8-disulfonic acid] | [2-Q, 4-Q, aniline] | Orange |
| 6 | [structure: 1-sulfo-5-sulfo-naphthyl-2-azo-1-hydroxy-8-amino-naphthalene-3,5-disulfonic acid] | [3-Q, 4-Q, aniline] | Bluish red |

-continued

| No. | A | B | Shade |
|-----|---|---|-------|
| 7 | 2-naphthalenesulfonic acid (SO₃H at position 1) azo-linked to 1-hydroxy-8-amino-3,6-disulfonic acid naphthalene (with SO₃H on coupler ring) | 2,4-di-Q aniline (H₂N–C₆H₃(Q)₂, Q at 2,4) | Bluish red |
| 8 | 5-(propionylamino)-4-hydroxy-7-sulfo-naphthalene (H₅C₂C(O)NH–, HO₃S–) azo-linked to 2-sulfo-5-amino-phenyl (SO₃H, NH₂; SO₃H on naphthalene coupler) | 2,4-di-Q aniline | Red |
| 9 | 5-benzamido-4-hydroxy-7-sulfo-naphthalene (PhC(O)NH–, SO₃H on naphthalene, extra SO₃H) azo-linked to 2,4-disulfo-5-amino-phenyl | 2,4-di-Q aniline | Red |
| 10 | 2,5-disulfophenyl azo-linked to 1-hydroxy-8-(4-aminobenzamido)-3,6-disulfo-naphthalene | 2,4-di-Q aniline | Red |
| 11 | 2,5-disulfophenyl azo-linked to 1-hydroxy-8-(4-aminobenzamido)-3,6-disulfo-naphthalene (isomer) | 2,4-di-Q aniline | — |
| 12 | 3,6-disulfo-naphthalene (HO₃S at 1 and ... ) azo-linked to 4-amino-2-(NHCONH₂)-phenyl; naphthalene bears SO₃H groups | 2,4-di-Q aniline | Yellow |
| 13 | 1,5-disulfo-naphthalene azo-linked to 4-amino-2-(NHCOCH₃)-phenyl | 2,5-di-Q aniline | Yellow |

-continued

| No. | A | B | Shade |
|-----|---|---|-------|
| 14 | [Cu-complexed azo dye with COO, SO3H, NH-N=C groups, phenyl-SO3H, and aminophenol-SO3H with NH2] | [H2N-phenyl with two Q substituents at 2,5-positions] | Blue |
| 15 | [Cu-complexed azo dye similar to 14 but with plain phenyl group instead of phenyl-SO3H] | [H2N-phenyl with two Q substituents at 2,5-positions] | Blue |
| 16 | [Cu-complexed azo dye with COO, SO3H, NH-N=C, phenyl group; aminophenol with single SO3H] | [H2N-phenyl with two Q substituents at 3,4-positions] | Blue |
| 17 | [Bis-azo naphthalene dye: HO3S-phenyl-N=N-(NH2,OH-naphthalene-disulfonic)-N=N-phenyl(SO3H, NH2)] | [H2N-phenyl with two Q substituents at 3,4-positions] | Navy blue |
| 18 | [Anthraquinone dye with NH2, SO3H, and NH-phenyl(SO3H, NH2) substituents] | [H2N-phenyl with two Q substituents at 2,5-positions] | Blue |
| 19 | [Anthraquinone dye with NH2, SO3H, and NHCH2CH2NHCH3 substituents] | [H2N-phenyl with two Q substituents at 3,4-positions] | Blue |

-continued
| No. | A | B | Shade |
|---|---|---|---|
| 20 | 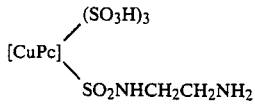 | 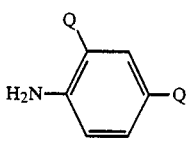 | Turquoise blue |
| 21 | 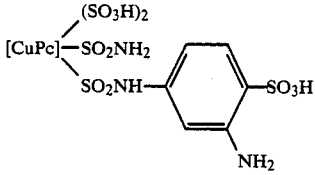 | 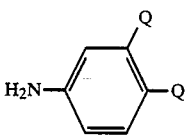 | Turquoise blue |
| 22 | 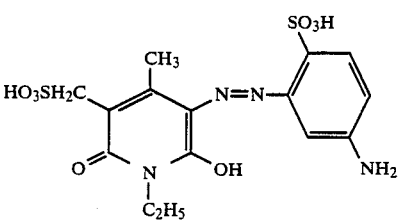 | 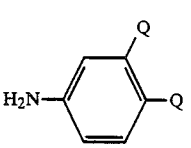 | Yellow |
| 23 | 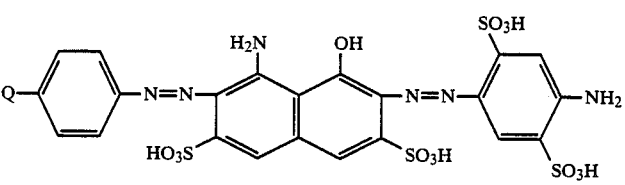 | 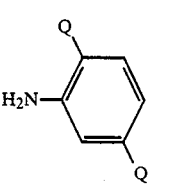 | Navy blue |
| 24 | 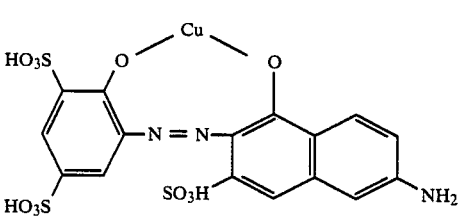 | 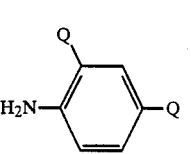 | Ruby |
| 25 | 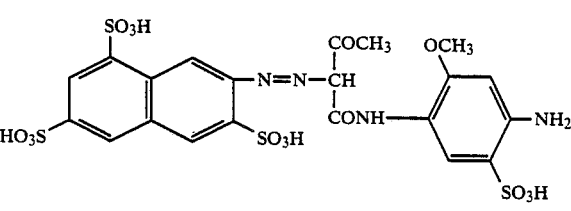 | 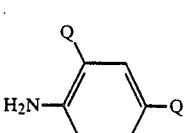 | Yellow |
| 26 | 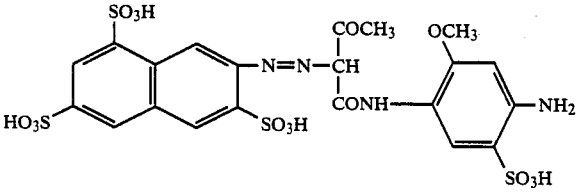 | 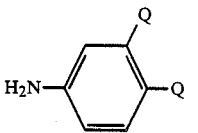 | Yellow |
| 27 | 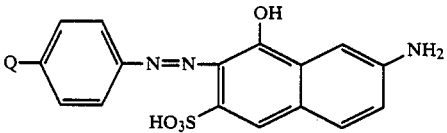 | 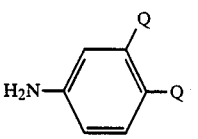 | Orange |

| No. | A | B | Shade |
|---|---|---|---|
| 28 | (structure: 3-sulfoanilino-naphthol with azo to 2-sulfo-5-amino-phenyl) | H₂N–C₆H₃(Q)(Q) | Brown |
| 29 | (structure: disazo naphthalene-sulfonic acid dye with OCH₃, CH₃, OH, NH₂) | H₂N–C₆H₃(Q)(Q) | Blue |
| 30 | (structure: disazo naphthalene with CH₃ and NH₂ terminal) | H₂N–C₆H₃(Q)(Q) | Reddish brown |
| 31 | (structure: pyridone azo with SO₃H, NH₂, N–C₂H₅) | H₂N–C₆H₃(Q)(Q) | Yellow |
| 32 | (structure: cyano-pyridone azo with N–C₂H₄NH₂) | H₂N–C₆H₃(Q)(Q) | Yellow |
| 33 | (structure: pyrazolone azo with aminomethyl naphthalene and sulfophenyl) | H₂N–C₆H₃(Q)(Q) | Yellow |
| 34 | (structure: pyrazolone azo with sulfophenyl) | H₂N–C₆H₃(Q)(Q) | Yellow |
| 35 | (structure: naphthalenedisulfonic acid azo with OCH₃, CH₃, NH₂) | H₂N–C₆H₃(Q)(Q) | Yellow |

-continued

| No. | A | B | Shade |
|---|---|---|---|
| 36 | (naphthalene with SO₃H, SO₃H)—N=N—(naphthalene with OH, HO₃S, NH₂) | 2,4-diQ aniline (H₂N-C₆H₃(Q)(Q)) | Orange |
| 37 | (naphthalene with HO₃S, OH, NH-C₂H₅)—N=N—(benzene with SO₃H, NH₂) | 2,4-diQ aniline | Red |
| 38 | (naphthalene with SO₃H, SO₃H)—N=N—(naphthalene with OH, NH₂, HO₃S, SO₃H)—N=N—(benzene with HO₃S, NH₂) | 2,4-diQ aniline | Navy blue |
| 39 | (naphthalene with SO₃H, H₂NCH₂)—N=N—(naphthalene with OH, NHCO-phenyl, HO₃S, SO₃H) | 3,4-diQ aniline | Red |
| 40 | (naphthalene with SO₃H, H₂NCH₂)—N=N—(naphthalene with OH, NHCO-phenyl, HO₃S, SO₃H) | 2,5-diQ aniline | Red |
| 41 | (naphthalene with HO₃S, H₂N, O—Cu—O)—N=N—(naphthalene with NH₂, SO₃H, SO₃H) | 2,5-diQ aniline | Blue |

-continued

| No. | A | B | Shade |
|---|---|---|---|
| 42 | [structure with SO₃H, O—Cu—O, N=N, CH₃, HO₃S, NH, CH₃] | [aniline with H₂N and two Q groups] | Navy blue |
| 43 | [naphthalene structure with SO₃H groups, N=N linkages, NH₂, SO₃H] | [aniline with H₂N and two Q groups] | Brown |

EXAMPLE 3

Examples 1 and 2 were repeated, provided that cyanuric fluoride was used in an amount equimolor to the cyanuric chloride used in the preceding Examples, thereby obtaining the corresponding triazine compound.

EXAMPLE 4

Using the compounds described below, a third condensation with the triazine compounds obtained in Examples 2 and 3 was carried out to obtain the corresponding desired triazine compound.

Aniline: N-Methylaniline: N-Ethylaniline: Aniline-2-,3- or 4-sulfonic acid: 2-, 3- or 4-Chloro-N-methylaniline: Taurine: 2-,3- or 4-Chloro-N-ethylaniline: N-Methyltaurine: Mono- or diethanolamine: Phenol: Ammonia: Methanol: β-Ethoxyethanol:

The above described compounds can be subjected to condensation with the compound shown in the column A of the preceding Examples prior to the condensation using the compound shown in the column B, thereby also obtaining the desired triazine compound.

EXAMPLE 5

Example 2 was repeated, provided that the compound shown in the column A was used in the amount two times that in Example 2 to perform the first and second condensations, followed by the third condensation with the compound shown in the column B, whereby the compound corresponding to the aforementioned formula (IV) was obtained.

EXAMPLE 6

Each triazine compound obtained in Examples 1, 2 and 3 was additionally subjected to condensation with the diamine compound shown below in an amount of a half molar ratio, whereby the compound corresponding to the aforementioned formula (VI) was obtained.

Ethylenediamine: Metamine: Paramine: m- or p-Phenylenediamine-sulfonic acid: 2,4,6-Trimethyl-3,5-diaminobenzenesulfonic acid: 4,4'-Diaminostilbene: 4,4'-Diaminodiphenylurea: Piperazine:

EXAMPLE 7

Sodium salt of 1-amino-8-hydroxy-2,7-bis(5-amino-2-sulfophenylazo)naphthalene-3,6-disulfonic acid (71.5 parts) was dissolved in water (1000 parts), and cyanuric chloride (37.0 parts) was added thereto. The mixture was stirred at 0° to 5° C., while controlling the pH within 2 to 5, thereby completing a first condensation. Successively, 1-aminobenzene-3,4-di(β-sulfatoethylsulfone) (93.8 parts) was added to the above reaction mixture, and the resulting mixture was stirred at 40° to 60° with a pH of 4 to 6 to complete a second condensation. Sodium chloride was added to the reaction mixture, and the precipitate was collected on a filter, washed and dried to obtain a triazine compound of the following formula in a free acid form.

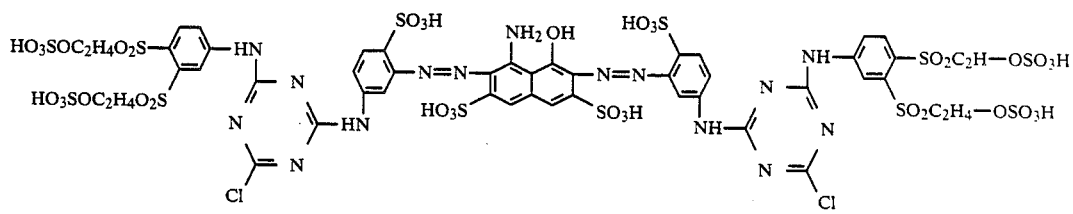

(λmax 620 nm)

EXAMPLE 8

Example 7 was repeated, provided that compounds as shown in columns A and B of the following table were used in place of the 1-Amino-8-hydroxy-2,7-bis(5-amino-2-sulfophenylazo)naphthalene-3,6-disulfonic acid and 1-aminobenzene-3,4-di(β-sulfatoethylsulfone)

used in Example 7, respectively, to obtain the corresponding triazine compound, which gave a dyed product of a shade as shown in the right column. In the table, Q means β-sulfatoethylsulfonyl, which can be replaced by vinylsulfonyl or a group convertible to the vinylsulfonyl by the action of an alkali.

| No. | A | B | Shade |
|---|---|---|---|
| 1 | [naphthalene with SO₃H, HO₃S, H₂NCH₂ groups azo-linked to a substituted benzene bearing COCH₃, OCH₃, CONH, NH₂, SO₃H] | 2,4-bis(Q)aniline (H₂N–C₆H₃(Q)₂) | Yellow |
| 2 | [naphthalene with SO₃H, H₂NCH₂ azo-linked to pyrazolone bearing COOH, OH, N-phenyl-3-NH₂] | 2,4-bis(Q)aniline | Yellow |
| 3 | [benzene with SO₃H, H₂N azo-linked to benzene with OCH₃, NH₂, CH₃] | 2,4-bis(Q)aniline | Yellow |
| 4 | [H-acid type: central naphthalene (OH, NH₂, HO₃S, SO₃H) bis-azo-linked to two naphthalenes each with SO₃H and H₂NCH₂/CH₂NH₂] | 2,4-bis(Q)aniline | Navy blue |
| 5 | [Cu-formazan complex: benzene-COO–Cu–O-benzene(NH₂, SO₃H), with N=N–C(–C₆H₄SO₃H)=N–N, H₂N and NH substituents] | 2,4-bis(Q)aniline | Blue |
| 6 | [dichloro-dioxazine: central dioxazine with two Cl, bearing SO₃H, H₂NC₂H₄NH on one side, and SO₃H, NHC₂H₄NH₂ on the other] | 2,4-bis(Q)aniline | Blue |
| 7 | | | |

| No. | A | B | Shade |
|---|---|---|---|
| 7 | [CuPc]((SO$_3$H)$_2$/(SO$_2$NH-C$_6$H$_3$(SO$_3$H)(NH$_2$)$_2$)$_2$) with SO$_3$H, NH$_2$ substituents | H$_2$N–C$_6$H$_3$(Q)$_2$ (2,4-) | Turquoise blue |
| 8 | Cr complex of bis(2-carboxyphenylazo-1-hydroxy-6-amino-3-sulfonaphthalene) | H$_2$N–C$_6$H$_3$(Q)$_2$ (2,5-) | Brown |
| 9 | 3-amino-6-sulfophenylazo-1-hydroxy-8-(3-aminobenzoylamino)-3,6-disulfonaphthalene | H$_2$N–C$_6$H$_3$(Q)$_2$ (2,4-) | Red |
| 10 | bis(aminoaryl)amino-dichloro-benzoquinone-diimine disulfonic acid derivative | H$_2$N–C$_6$H$_3$(Q)$_2$ (2,4-) | Blue |
| 11 | 5-amino-1-sulfo-2-naphthylazo-1-hydroxy-8-amino-3,6-disulfonaphthalene (with H$_2$NCH$_2$) | H$_2$N–C$_6$H$_3$(Q)$_2$ (2,4-) | Red |
| 12 | bis(piperazinyl-sulfophenylamino)-dichloro-benzoquinonediimine | H$_2$N–C$_6$H$_3$(Q)$_2$ (2,4-) | Blue |
| 13 | | | |

| No. | A | B | Shade |
|---|---|---|---|
| | 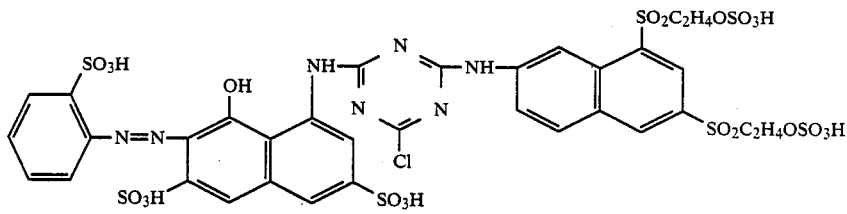 | | Blue |

EXAMPLE 9

Using each triazine compound obtained in Examples 7 and 8, a third condensation similar to that of Example 4 was carried out to obtain the corresponding desired triazine compound.

EXAMPLE 10

Successively, 2-aminonaphthalene-6,8-di(β-sulfatoethylsulfone) (52.1 parts) was added to the above reaction mixture, and the resulting mixture was stirred at 40° to 50° C. within a pH of 4 to 5 to complete a second condensation. Sodium chloride was added to the reaction mixture, and the precipitate was collected on a filter, washed and dried to obtain a triazine compound of the following formula in a free acid form.

(λmax 545 nm)

Examples 7 and 8 were repeated, provided that cyanuric fluoride was used in an amount equimolar to the cyanuric chloride used in the preceding Examles, thereby obtaining the corresponding desired triazine compound.

EXAMPLE 11

Sodium salt of 1-amino-8-hydroxy-7-(o-sulfophenylazo)naphthalene-3,6-disulfonic acid (50.4 parts) was dissolved in water (500 parts), and cyanuric chloride (18.5 parts) was added thereto. The mixture was stirred at 0° to 5° C., while controlling the pH within 2 to 3, to complete a first condensation.

EXAMPLE 12

Example 11 was repeated, provided that compounds as shown in columns A and B of the following table were used in place of 1-amino-8-hydroxy-7-(o-sulfophenylazo)naphthalene-3,6-disulfonic acid and 2-aminonaphthalene-6,8-di(β-sulfatoethylsulfone), respectively, thereby obtaining the corresponding triazine compound, which gave a dyed product of a shade as shown in the right column. In the table, Q means β-sulfatoethylsulfonyl, which can be replaced by vinylsulfonyl or a group convertible to the vinylsulfonyl by the action of an alkali.

| No. | A | B | Shade |
|---|---|---|---|
| 1 | | | Yellowish red |
| 2 | | | Bluish red |

-continued

| No. | A | B | Shade |
|---|---|---|---|
| 3 | 4-methoxy-2-sulfophenyl-azo-(1-hydroxy-8-sulfo-7-(N-methylamino)-3-sulfo)naphthalene | 6-amino-naphthalene (Q at 5,7) | Orange |
| 4 | 5-Q-2-sulfophenyl-azo-(1-hydroxy-8-amino-5-sulfo-3-sulfo)naphthalene | 6-amino-7-sulfo-naphthalene (Q at 5,7) | Red |
| 5 | 1,5-disulfonaphth-2-yl-azo-(1-hydroxy-8-sulfo-3-sulfo-8a?)naphthalene | 6-amino-naphthalene (Q at 5,7) | Red |
| 6 | 4-methoxy-2-sulfophenyl-azo-(1-hydroxy-6-amino-3-sulfo)naphthalene | 2-amino-1-sulfo-naphthalene (Q at 5,7) | Orange |
| 7 | 3,6-disulfo-7-azo-naphthalene–(2,4-diamino-NHCONH₂-phenyl) | 6-amino-naphthalene (Q at 5,7) | Yellow |
| 8 | 1-sulfonaphth-2-yl-azo-(1-hydroxy-8-amino-3,6-disulfo)naphthalene | 6-amino-naphthalene (Q at 5,7) | Bluish red |
| 9 | 8-benzamido-1-hydroxy-3-sulfo-5-sulfo-naphth-2-yl-azo-(2,5-disulfo-4-amino)phenyl | 6-amino-naphthalene (Q at 5,7) | Red |
| 10 | 2,5-disulfophenyl-azo-(1-hydroxy-8-(NHCO-4-aminophenyl)-3,6-disulfo)naphthalene | 6-amino-naphthalene (Q at 5,7) | Red |

-continued

| No. | A | B | Shade |
|---|---|---|---|
| 11 | (structure: naphthalene with OH, HO₃S, SO₃H, NHCO-C₆H₄-NH₂, and azo-linked benzene with SO₃H, SO₃H) | (naphthalene with two Q and NH₂) | Red |
| 12 | (structure: naphthalene with NH₂, OH, HO₃S, SO₃H, azo-linked to HO₃S-C₆H₄ on one side and to SO₃H/NH₂-benzene on other) | (naphthalene with two Q and NH₂) | Navy blue |
| 13 | (anthraquinone with NH₂, SO₃H, SO₃H, NH-C₆H₃-NH₂) | (naphthalene with two Q and NH₂) | Blue |
| 14 | (naphthalene with SO₃H, SO₃H, azo-linked to benzene with NH₂, NHCOCH₃) | (naphthalene with two Q and NH₂) | Yellow |
| 15 | (pyridone: HO₃SH₂C, CH₃, N-C₂H₅, OH, O, azo-linked to benzene with SO₃H, NH₂) | (naphthalene with two Q and NH₂) | Yellow |
| 16 | (naphthalene with H₂N, OH, HO₃S, SO₃H, azo-linked Q-C₆H₄ and SO₃H/NH₂/SO₃H-benzene) | (naphthalene with two Q and NH₂) | Navy blue |
| 17 | (naphthalene with OH, NH₂, HO₃S, azo-linked Q-C₆H₄) | (naphthalene with two Q, NH₂, SO₃H) | Orange |
| 18 | (naphthalene with OH, SO₃H, NH-C₆H₄-SO₃H, azo-linked benzene with SO₃H, NH₂) | (naphthalene with two Q, NH₂, SO₃H) | Brown |

-continued
| No. | A | B | Shade |
|---|---|---|---|
| 19 | 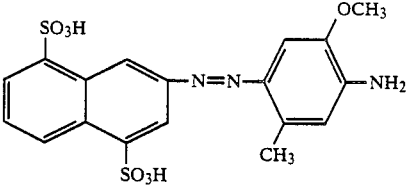 | 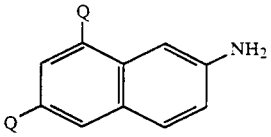 | Yellow |
| 20 | 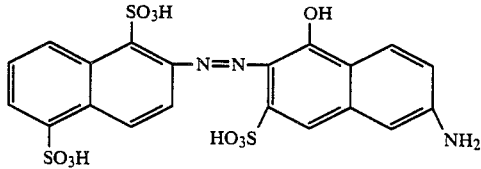 | 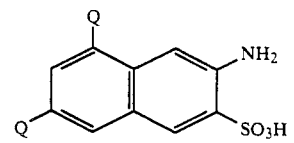 | Orange |
| 21 | 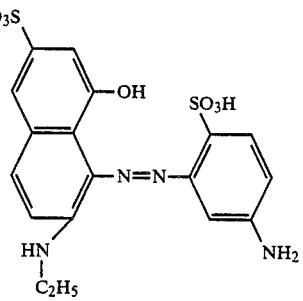 | 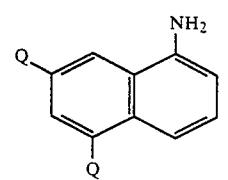 | Red |
| 22 | 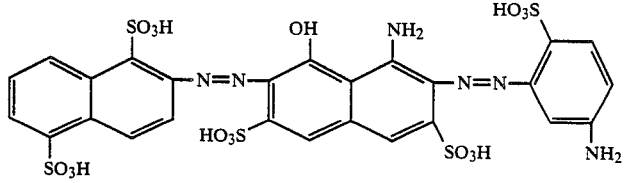 | 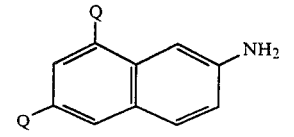 | Navy blue |
| 23 | 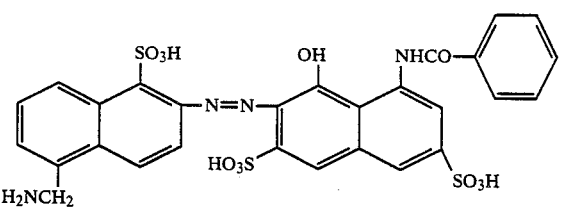 | 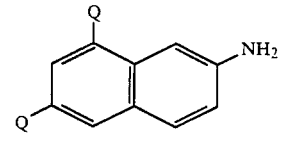 | Red |
| 24 | 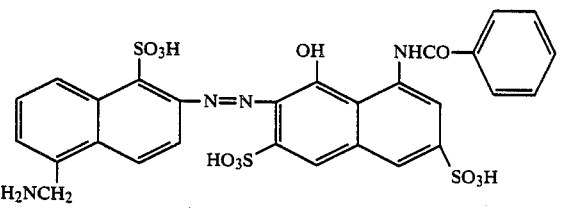 | 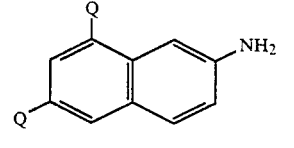 | Red |
| 25 | 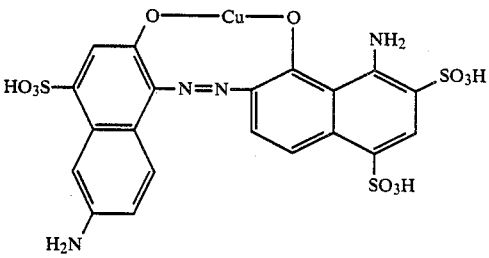 | 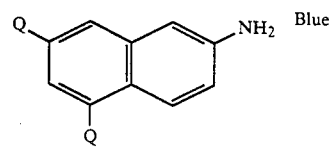 | Blue |

-continued

| No. | A | B | Shade |
|---|---|---|---|
| 26 | 8-SO₃H naphthalene-3-yl—N=N—(1,4-naphthyl with 4-SO₃H, 7-SO₃H)—N=N—(4-amino-8-SO₃H-naphthyl) | 3-Q, 7-Q, 6-NH₂ naphthalene | Brown |
| 27 | 2,5-disulfo-phenyl—N=N—(2-methyl-4-O-Cu complex phenyl)—N=N—(1-O-, 3-SO₃H, 6-NHCH₃ naphthyl) | 4-Q, 7-Q, 6-NH₂ naphthalene | Navy blue |
| 28 | 8-SO₃H, 4-SO₃H-naphthalen-3-yl—N=N—(1,4-naphthyl, 7-SO₃H)—N=N—(2-methyl-4-amino-phenyl) | 3-Q, 7-Q (with NH₂), 8-Q naphthalene | Reddish brown |
| 29 | 1,3,6-trisulfo-naphthalen-7-yl—N=N—(2-methyl-4-OCH₃ phenyl)—N=N—(1-OH, 3-SO₃H, 8-NH₂, 6-SO₃H naphthyl) | 4-Q, 7-Q, 6-NH₂ naphthalene | Blue |
| 30 | 4-methyl-1-ethyl-6-OH-2-oxo-pyridinyl—N=N—(2-SO₃H, 5-NH₂ phenyl) | 4-Q, 7-Q, 6-NH₂ naphthalene | Yellow |
| 31 | 8-(H₅C₂CONH), 1-OH, 6-SO₃H, 3-naphthyl—N=N—(2-SO₃H, 5-NH₂ phenyl) | 4-Q, 7-Q, 6-NH₂ naphthalene | Red |
| 32 | Cu complex of salicylaldehyde hydrazone (HO₃S-phenyl-COO-Cu-O-phenyl-NH₂, with sulfo groups) | 4-Q, 7-Q, 6-NH₂ naphthalene | Blue |

-continued
| No. | A | B | Shade |
|---|---|---|---|
| 33 | 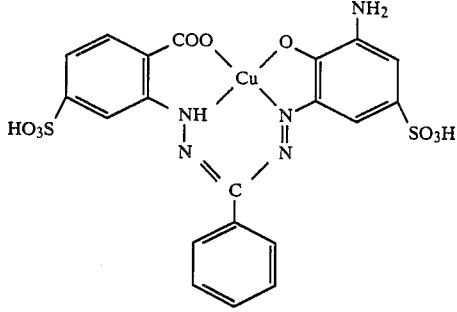 | 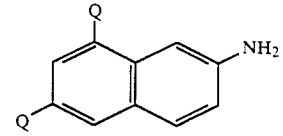 | Blue |
| 34 | 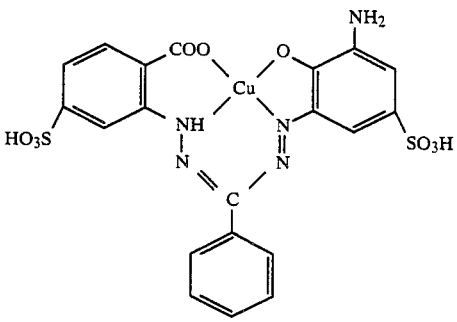 | 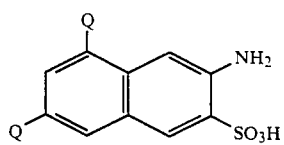 | Blue |
| 35 | 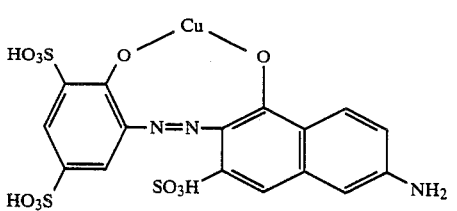 | 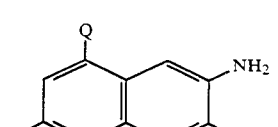 | Ruby |
| 36 | 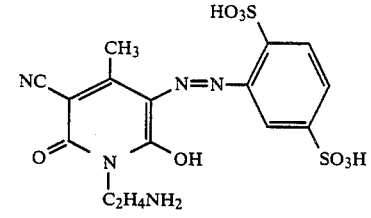 | 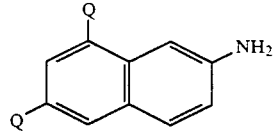 | Yellow |
| 37 | 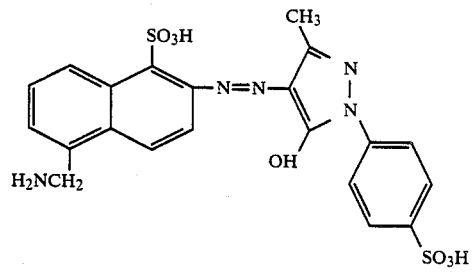 | 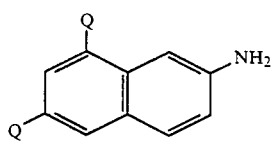 | Yellow |
| 38 | 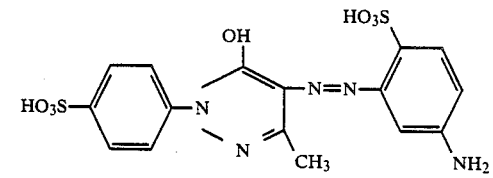 | 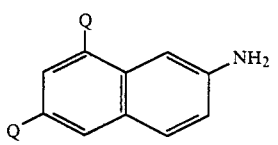 | Yellow |

| No. | A | B | Shade |
|---|---|---|---|
| 39 | 1-amino-4-(2-methylaminoethylamino)anthraquinone-2-sulfonic acid | 2-amino-naphthalene with 2 Q substituents | Blue |
| 40 | [CuPc]−(SO₃H)₃, SO₂NHCH₂CH₂NH₂ | 8-amino-naphthalene with 2 Q substituents | Turquoise blue |
| 41 | [CuPc]−(SO₃H)₂, SO₂NH₂, SO₂NH-(aminophenyl)-SO₃H | 3-amino-6-sulfo-naphthalene with 2 Q substituents | Turquoise blue |
| 42 | naphthalene trisulfonic acid azo coupling with COCH₃/CONH-(methoxy-amino-sulfophenyl) | 2-amino-naphthalene-1-sulfonic acid with 2 Q substituents | Yellow |
| 43 | naphthalene trisulfonic acid azo coupling with COCH₃/CONH-(methoxy-amino-sulfophenyl) | 2-amino-naphthalene with 2 Q substituents | Yellow |
| 44 | 2,5-disulfophenyl-azo-(4-amino-2-ureido)phenyl | 2-amino-naphthalene with 2 Q substituents | Yellow |

EXAMPLE 13

Examples 11 and 12 were repeated, provided that cyanuric fluoride was used in an amount equimolar to the cyanuric chloride used in Examples 11 and 12, thereby obtaining the corresponding desired triazine compound.

EXAMPLE 14

Each triazine compound obtained in Examples 12 and 13 was additionally subjected to third condensation with each compound described below, thereby obtaining the corresponding desired triazine compound.

Aniline: N-Methylaniline: N-Ethylaniline: Aniline-2-, 3- or 4-sulfonic acid: 2-, 3- or 4-Chloro-N-ethylaniline: 2-, 3- or 4-Chloro-N-methylaniline: Taurine: N-Methyltaurine: Mono- or diethanolamine: Phenol: Ammonia: Methanol: β-Ethoxyethanol:

The above described compounds can be subjected to condensation with the compound shown in the column A of the preceding Examples prior to the condensation using the compound shown in the column B, thereby obtaining also the desired triazine compound.

EXAMPLE 15

Example 12 was repeated, provided that the compound shown in the column A was used in an amount twice that of Example 12 to effect first and second condensations with cyanuric chloride or fluoride, followed by a third condensation with the compound shown in the column B, whereby the compound corresponding to the aforementioned formula (IV) was obtained.

EXAMPLE 16

Each triazine compound obtained in Examples 11, 12 and 13 was additionally subjected to condensation with each diamine compound described below in an amount of a half molar ratio, whereby the desired triazine compound corresponding to the aforementioned formula (VI) was obtained.

sively, 2-aminonaphthalene-6,8-di(β-sulfatoethylsulfone) (104.2 parts) was added to the above reaction mixture, and the resulting mixture was stirred at 40° to 60° C. within a pH of 4 to 6 to complete a second condensation. The reaction mixture was mixed with sodium chloride, and the precipitate was collected on a filter, washed and dried to obtain a triazine compound of the following formula in a free acid form.

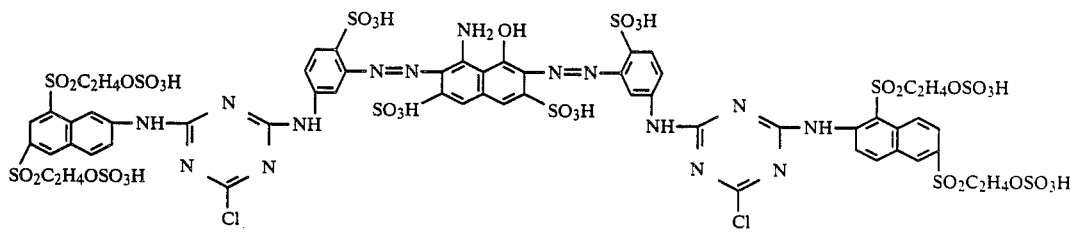

(λmax 620 nm)

Ethylenediamine: Metamine: Paramine: m- or p-Phenylenediaminesulfonic acid: 2,4,6-Trimethyl-3,5-diaminobenzenesulfonic acid: 4,4'-Diaminostilbene: 4,4'-Diaminodiphenylurea: Piperazine:

EXAMPLE 17

Sodium salt of 1-amino-8-hydroxy-2,7-bis(5-amino-2-sulfophenylazo)naphthalene-3,6-disulfonic acid (71.5 parts) was dissolved in water (1000 parts), and cyanuric chloride (37.0 parts) was added thereto, and the mixture was stirred at 0° to 5° C., while controlling the pH within 2 to 5, to complete a first condensation. Succes-

EXAMPLE 18

Example 17 was repeated, provided that compounds as shown in columns A and B of the following table were used in place of the 1-amino-8-hydroxy-2,7-bis(5-amino-2-sulfophenylazo)naphthalene-3,6-disulfonic acid and 2-aminonaphthalene-6,8-di(β-sulfatoethylsulfone), respectively, thereby obtaining the corresponding desired triazine compound. In the table, Q means β-sulfatoethylsulfonyl, which can be replace by vinylsulfonyl or a group convertible to the vinylsulfonyl by the action of an alkali.

| No. | A | B | Shade |
|---|---|---|---|
| 1 | (structure with dichloroquinone, SO₃H, NHC₂H₄NH₂ groups) | 6-aminonaphthalene-1,3-diol | Blue |
| 2 | [CuPc](SO₃H)₂(SO₂NH-C₆H₃(SO₃H)(NH₂))₂ | 6-aminonaphthalene-1,3-diol | Turquoise blue |
| 3 | Cr complex of bis-azo naphthol with salicylic acid | 5-aminonaphthalene-2,4-diol | Brown |
| 4 | (naphthol azo structure with SO₃H, NHCO, OH, NH₂ groups) | 6-aminonaphthalene-1,3-diol | Red |

-continued

| No. | A | B | Shade |
|---|---|---|---|
| 5 | (structure) | (structure) | Yellow |
| 6 | (structure) | (structure) | Yellow |
| 7 | (structure) | (structure) | Yellow |
| 8 | (structure) | (structure) | Navy blue |

-continued

| No. | A | B | Shade |
|---|---|---|---|
| 9 | | | Blue |
| 10 | | | Blue |
| 11 | | | Red |
| 12 | | | Blue |

-continued

| No. | A | B | Shade |
|---|---|---|---|
| 13 | ![structure: dichloro-quinone-diimine linked to two amino-sulfonaphthyl groups] | ![structure: naphthalene with SO₃H, NH₂, and two Q substituents] | Blue |

EXAMPLE 19

Using each triazine compound obtained in Examples 17 and 18, a third condensation similar to that of Example 14 was carried out to obtain the corresponding desired triazine compound.

EXAMPLE 20

Examples 17 and 18 were repeated, provided that cyanuric fluoride was used in an amount equimolar to the cyanuric chloride used in Examples 17 and 18, thereby obtaining the corresponding desired triazine compound.

DYEING EXAMPLE 1

The triazine compounds (each 0.3 part) obtained in Examples 1 to 20 were respectively dissolved in water (200 parts). Sodium sulfate (10 parts) and cotton (10 parts) was added thereto, and the dyebath was heated to 60° C. Twenty minutes thereafter, sodium carbonate (4 parts) was added thereto, and dyeing was continued for 1 hour at that temperature. Thereafter, the cotton taken out of the bath was washed with water and soaped to obtain a dyed product excellent in fastness properties with superior dye performance. Even when the dyebath conditions including temperatures, bath ratio and amount of the inorganic salt were varied to some extent, a dyed product of invariable quality was obtained with superior reproducibility.

DYEING EXAMPLE 2

Composition of color paste:

| Each triazine compound obtained in Examples 1 to 20 | 5 parts |
| --- | --- |
| Urea | 5 parts |
| Sodium alginate (5%), thickener | 50 parts |
| Hot water | 25 parts |
| Sodium hydrogencarbonate | 2 parts |
| Balance (water) | 13 parts |

Mercerized cotton broad cloth was printed with the color paste of the above composition, pre-dried, steamed at 100° C. for 5 minutes, washed with hot water, soaped, again washed with hot water and dried, thereby obtaining a printed product excellent in fastness properties with superior dye performance.

DYEING EXAMPLE 3

Each triazine compound obtained in Examples 1 to 20 (25 parts) was dissoved in hot water, and the solution was cooled to 25° C. Aqueous 32.5% sodium hydroxide solution (5.5 parts) and 50° Be' water glass (150 parts) were added thereto, and water was added to make the whole 1000 parts at 25° C. to obtain a padding liquor. Immediately thereafter, cotton cloth was padded with the padding liquor and batched up, and the cloth wrapped tightly with a polyethylene film was allowed to stand in a room kept at 20° C.

Above manner was repeated to obtain a padded cotton cloth, which was then wrapped tightly with a polyethylene film, and allowed to stand in a room kept at 5° C.

Both cloths were allowed to stand for 20 hours, and thereafter washed with cold water and then hot water, soaped with a boiling detergent, washed with cold water and then dried.

There was observed almost no difference in their color shade and depth between the dyed products obtained after standing at 5° C. and 20° C. each for 20 hours. In this cold batch-up dyeing method, each triazine compound was found to have superior build-up property.

We claim:

1. A triazine compound represented by the following formula,

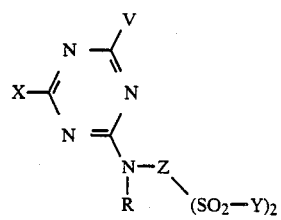

wherein R is hydrogen or $C_{1-4}$ alkyl unsubstituted or substituted by hydroxy, cyano, $C_{1-4}$ alkoxy, halogeno, carboxy, carbamoyl, $C_{1-4}$ alkoxycarbonyl, $C_{1-4}$ alkylcarbonyloxy, sulfo or sulfamoyl, Y is vinyl or —CH$_2$CH$_2$L in which L is a group splittable by the action of an alkali, Z is phenylene or naphthylene unsubstituted or substituted once by sulfo, X is halogeno, $C_{1-4}$ alkoxy, sulfoethylamino, N-methylsulfoethylamino, mono- or di-ethanolamino, β-ethoxyethanolamino, ethyanolamino, phenoxy, anilino unsubstituted or substituted by sulfo, carboxy, chloro, $C_{1-4}$ alkyl or $C_{1-4}$ alkoxy, or a group of the formula (1),

wherein $R_1$ is hydrogen or $C_{1-4}$ alkyl unsubstituted or substituted by hydroxy, cyano, $C_{1-4}$ alkoxy, halogeno, carboxy, carbamoyl, $C_{1-4}$ alkoxycarbonyl, $C_{1-4}$ alkylcarbonyloxy, sulfo or sulfamoyl, $D_1$ is a moiety of an anionic dye having —SO$_3^\ominus$ as the anion selected from metal-containing and metal-free azo, anthraquinone, metal-containing phthalocyanine, metal-containing formazane, dioxazine and stilbene dyes, and $Y_1$ is vinyl or —CH$_2$CH$_2$L in which L is as defined above, and V is a group of formula (2),

wherein $R_2$ is hydrogen or $C_{1-4}$ alkyl unsubstituted or substituted by hydroxy, cyano, $C_{1-4}$ alkoxy, halogeno, carboxy, carbamoyl, $C_{1-4}$ alkoxycarbonyl, $C_{1-4}$ alkylcarbonyloxy, sulfo or sulfamoyl, $D_2$ is a moiety of an anionic dye having —SO$_3^\ominus$ as the anion selected from metal-containing phthalocyanine, metal-containing formazane, dioxazine and stilbene dyes, and $Y_2$ is vinyl or —CH$_2$CH$_2$L in which L is as defined above, or the formula (3),

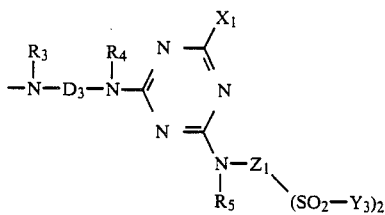 (3)

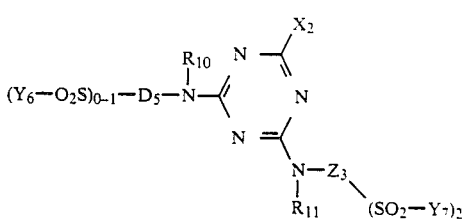

wherein $R_3$, $R_4$ and $R_5$ independently of one another are each hydrogen or $C_{1-4}$ alkyl unsubstituted or substituted by hydroxy, cyano, $C_{1-4}$ alkoxy, halogeno, carboxy, carbamoyl, $C_{1-4}$ alkoxycarbonyl, $C_{1-4}$ alkylcarbonyloxy, sulfo or sulfamoyl, $D_3$ is a moiety of an anionic dye having $—SO_3^{\ominus}$ as the anion selected from metal-containing and metal-free azo, anthraquinone, metal-containing phthalocyanine, metal-containing formazane, dioxazine and stilbene dyes, $X_1$ is halogeno, $C_{1-4}$ alkoxy, sulfoethylamino, N-methyl-sulfoethylamino, mono- or diethanolamino, β-ethoxyethanolamino, phenoxy, anilino unsubstituted or substituted by sulfo, carboxy, chloro, $C_{1-4}$ alkyl or $C_{1-4}$ alkoxy, $Y_3$ is vinyl or $—CH_2CH_2L$ in which L is as defined above, and $Z_1$ is phenylene or naphthylene unsubstituted or substituted once by sulfo, or the formula (4)

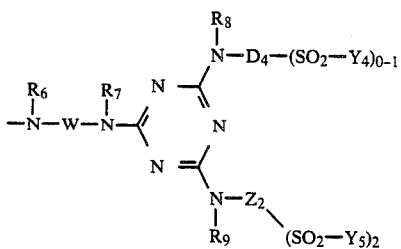 (4)

wherein W is a divalent group selected from $C_{2-6}$ alkylene, phenylene, mono- or di-sulfophenylene, 1,3,5-trimethyl-4-sulfo-2,6-phenylene, 6-substituted-1,3,5-triazine-2,4-di-yl or stilben-4,4'-di-yl, $R_6$, $R_7$, $R_8$ and $R_9$ independently of one another are each hydrogen or $C_{1-4}$ alkyl unsubstituted or substituted by hydroxy, cyano, $C_{1-4}$ alkoxy, halogeno, carboxy, carbamoyl, $C_{1-4}$ alkoxycarbonyl, $C_{1-4}$ alkylcarbonyloxy, sulfo or sulfamoyl, $X_2$ is phenylene or naphthylene unsubstituted or substituted once by sulfo, $D_4$ is a moiety of an anionic dye having $—SO_3^{\ominus}$ as the anion selected from metal-containing and metal-free azo, anthraquinone, metal-containing phthalocyanine, metal-containing formazane, dioxazine and stilbene dyes, and $Y_4$ and $Y_5$ independently of one another are each vinyl or $—CH_2CH_2L$ in which L is as defined above.

2. A triazine compound according to claim 1, wherein R, $R_1$, $R_2$, $R_3$, $R_4$, $R_5$, $R_6$, $R_7$, $R_8$ and $R_9$ independently of one another are each hydrogen, methyl or ethyl.

3. A triazine compound according to claim 1, wherein $X_1$ is chloro, fluoro or unsubstituted or substituted anilino.

4. A triazine compound according to claim 1, wherein the compound is represented by the following formula, wherein $R_{10}$ and $R_{11}$ independently of one another are each hydrogen or unsubstituted or substituted alkyl, $X_2$ is chloro, fluoro, unsubstituted or substituted aliphatic or aromatic amino, $C_{1-4}$ alkoxy or unsubstituted or substituted phenoxy, $Y_6$ and $Y_7$ are independently of one another are each vinyl or $—CH_2CH_2L$ in which L is as defined in claim 1, and $D_5$ is a dye moiety.

5. A triazine compound according to claim 1, wherein the compound is represented by the following formula,

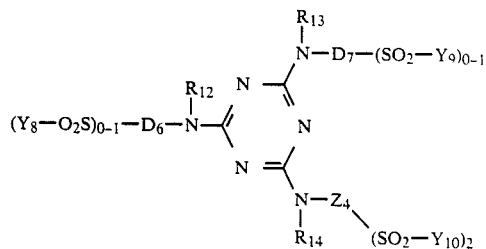

wherein $R_{12}$, $R_{13}$ and $R_{14}$ independently of one another are each hydrogen or unsubstituted or substituted alkyl, $Y_8$, $Y_9$ and $Y_{10}$ independently of one another are each vinyl or $—CH_2CH_2L$ in which L is as defined in claim 1, and $D_6$ and $D_6$ and $D_7$ independently of one another are each a dye moiety.

6. A triazine compound according to claim 1, wherein the compound is represented by the following formula,

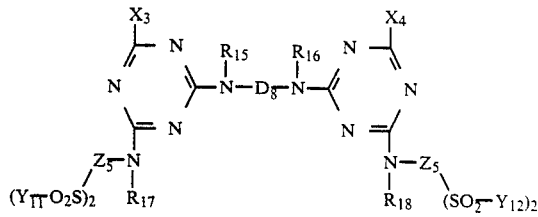

wherein $R_{15}$, $R_{16}$, $R_{17}$ and $R_{18}$ are independently of one another are each hydrogen or unsubstituted or substituted alkyl, $X_3$ and $X_4$ independently of one another are each chloro, fluoro, unsubstituted or substituted aliphatic or aromatic amino, $C_{1-4}$ alkoxy or unsubstituted or substituted phenoxy, $Y_{11}$ and $Y_{12}$ independently of one another are each vinyl or $—CH_2CH_2L$ in which L is as defined in claim 1, and $D_8$ is a dye moiety.

7. A triazine compound according to claim 6, where $X_3$ and $X_4$ are the same and chloro, fluoro or unsubstituted or substituted anilino.

8. A triazine compound according to claim 1, wherein the compound is represented by the following formula,

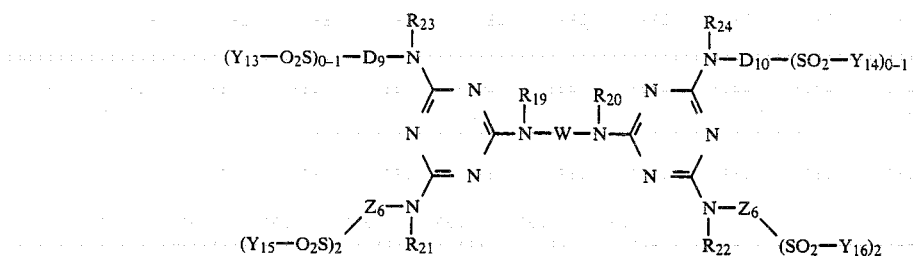
wherein $R_{19}$, $R_{20}$, $R_{21}$, $R_{22}$ $R_{23}$ and $R_{24}$ independently of one another are each hydrogen or unsubstituted or substituted alkyl, W is a divalent group, $Y_{13}$, $Y_{14}$, $Y_{15}$ and $Y_{16}$ independently of one another are each vinyl or —$CH_2CH_2L$ in which L is as defined in claim 1, and $D_9$ and $D_{10}$ independently of one another are each a dye moiety.
* * * * *